United States Patent
Milne et al.

(10) Patent No.: US 7,767,229 B1
(45) Date of Patent: Aug. 3, 2010

(54) USE OF POLY DIALLYAMINE POLYMERS

(76) Inventors: Paul E Milne, QinetiQ Malvern, St Andrews Road, Malvern, Worcs (GB) WR14 3PS; John W Goodby, University of Hull, School of Chemistry, Hull (GB) HU6 7RX; Alan W. Hall, University of Hull, School of Chemistry, Hull (GB) HU6 7RX; Keith M Blackwood, Senior Design Engineer, Optellios Inc, 250 Phillips Blvd., Ewing, NJ (US) 08618

( * ) Notice: Subject to any disclaimer, the term of this patent is extended or adjusted under 35 U.S.C. 154(b) by 887 days.

(21) Appl. No.: 10/130,246

(22) PCT Filed: Nov. 10, 2000

(86) PCT No.: PCT/GB00/04308

§ 371 (c)(1),
(2), (4) Date: Aug. 21, 2002

(87) PCT Pub. No.: WO01/36510

PCT Pub. Date: May 25, 2001

(30) Foreign Application Priority Data

Nov. 17, 1999 (GB) .................................. 9927088.6

(51) Int. Cl.
*A61K 9/14* (2006.01)
(52) U.S. Cl. ...................................................... 424/486
(58) Field of Classification Search .................... 424/78, 424/78.35, 78.08, 78.14, 78.15
See application file for complete search history.

(56) References Cited

U.S. PATENT DOCUMENTS

| | | | | |
|---|---|---|---|---|
| 2,921,006 | A * | 1/1960 | Schmitz et al. | ............. 522/142 |
| 3,957,699 | A | 5/1976 | Solomon et al. | |
| 4,759,923 | A * | 7/1988 | Buntin et al. | ............... 424/440 |
| 6,203,785 | B1 * | 3/2001 | Holmes-Farley et al. | . 424/78.18 |
| 6,726,905 | B1 * | 4/2004 | Mandeville et al. | ...... 424/78.35 |

FOREIGN PATENT DOCUMENTS

| | | | |
|---|---|---|---|
| EP | 0 296 622 A2 | | 12/1988 |
| JP | 62-257481 | | 11/1987 |
| WO | WO 98/29107 | * | 6/1998 |
| WO | 98/29107 | | 7/1998 |
| WO | WO 98/29107 | * | 7/1998 |
| WO | WO-9829107 | * | 7/1998 |
| WO | 99/22721 | | 5/1999 |
| WO | 99/22743 | | 5/1999 |
| WO | WO 99/22743 | * | 5/1999 |

OTHER PUBLICATIONS

McLean et al; "Cyclopolymerization. VI. Preparation and Properties of Crosslinked Polyamines by Cyclopolymerization"; J. Macromol. Sci. Chem. A 10(5), pp. 857-873, 1976; XP002068701.
Bolto et al; "Synthesis of Cross-Linked Polyallylamines Which Are Resistant to Sulfite Attack"; . Macromol. Sci. Chem. A 17(1), pp. 153-166; 1982, XP002068702.
Patent Abstract, JP 57047302; Ito Isao, "Preparation of Crosslinkable Electrolytic Polymer"; Mar. 18, 1982.
Patent Abstract, JP 020011358; Okamoto Masato; "Chemical for Ink Jet Recording Paper"; Jan. 5, 1990.

* cited by examiner

*Primary Examiner*—Carlos A Azpuru
(74) *Attorney, Agent, or Firm*—Nixon & Vanderhye P.C.

(57) ABSTRACT

A poly(diallylamine)polymer pharmaceutical composition or pharmaceutical derivate used to sequester bile acid and/or to reduce serum cholesterol levels. The polymer is derived from a monomer of formula Ia, where $R^6$ is a bridging group of valency r, and r is an integer of 3 or greater to provide a cross linked polymer, and all diallyl nitrogen atoms are linked to at least two further diallyl nitrogen atoms.

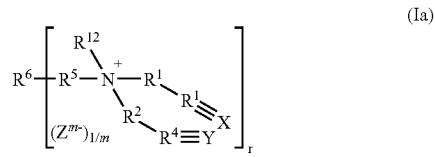

(Ia)

15 Claims, 1 Drawing Sheet

USE OF POLY DIALLYAMINE POLYMERS

Figure 1:
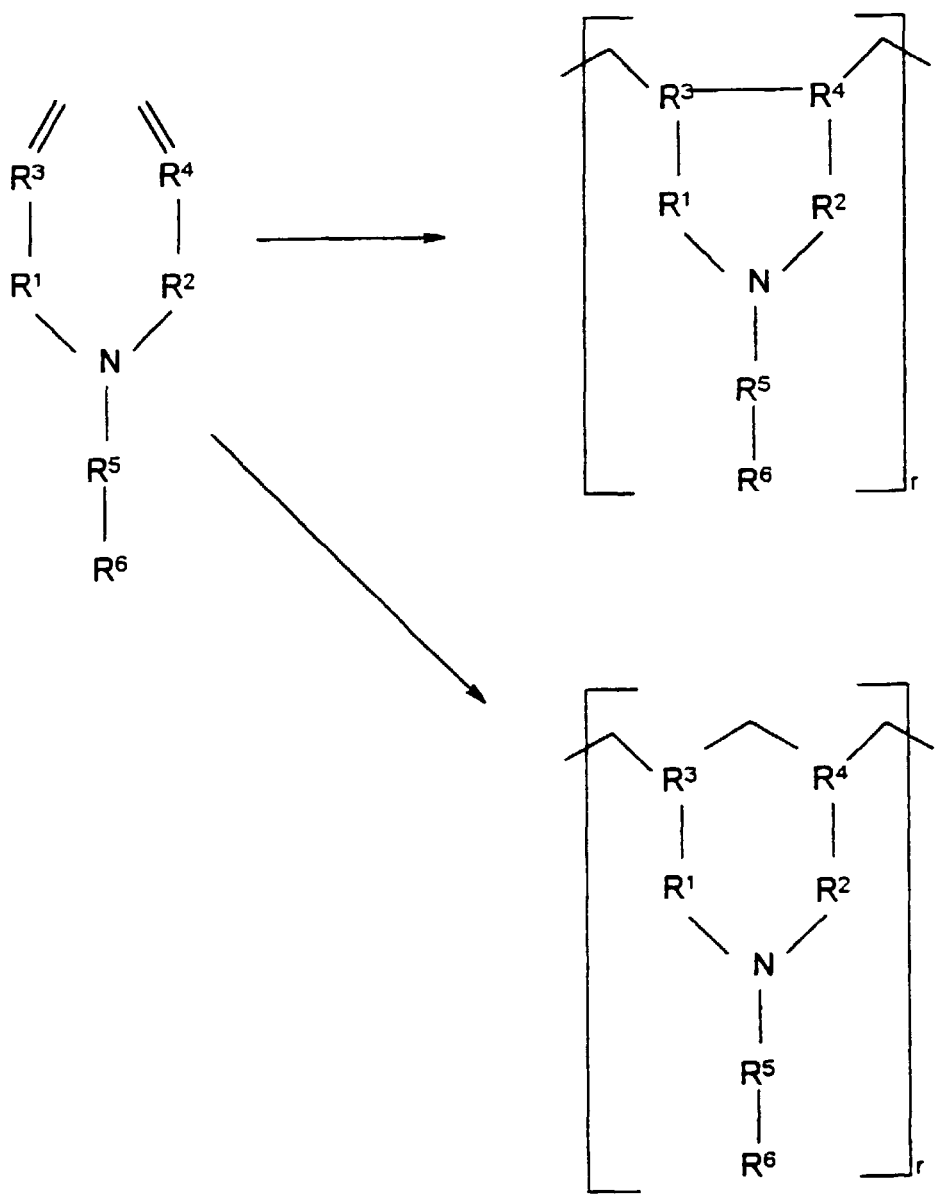

The present invention relates to the use of certain poly (diallylamine) polymers as bile acid removers.

Bile acid salts, produced in the body from cholesterol, aid the digestion of dietary fats. They are usually reabsorbed into the bloodstream following digestion, which helps to conserve serum cholesterol levels. The cholesterol level can therefore be reduced by hindering reabsorption of the bile acids. One way of doing this is to administer compounds which sequester the bile acids but cannot themselves be absorbed; the sequestered acids are then excreted and serum cholesterol is used up in the production of more bile acids.

WO 98/29107 describes certain poly(diallylamine)-based, hydrophobically-substituted bile acid sequestrants.

Our co-pending PCT application number PCT/GB99/02416 discloses certain diallylamine monomers and the polymers and copolymers derived from them.

According to a first aspect of the present invention, there is provided a poly(diallylamine) polymer comprising a repeat unit derived from a monomer of the general formula I below, or a pharmaceutically acceptable derivative of such a polymer, for use as a bile acid sequestrant/remover for administration to a human or animal patient, and/or for use in reducing serum cholesterol levels in a human or animal patient.

Derivatives of the polymer include for instance pharmaceutically acceptable salts thereof, co-ordination complexes for example with metal ions, hydrated forms, labelled forms for instance for use in diagnostic methods and pharmaceutical precursors which are convertible, either in vitro or in vivo, into the relevant polymer.

The polymer or derivative should ideally be in a form which is stable and non-absorbable in the patient, and of a molecular weight which enables it to reach the gastrointestinal tract and remain there sufficiently long for it to remove a significant amount of bile acid.

According to a second aspect, the invention provides the use of such a polymer or derivative in the preparation of a medicament for use as a bile acid sequestrant/remover for administration to a human or animal patient, and/or for use in reducing serum cholesterol levels in a human or animal patient.

Since the present invention is based on the first medical indication for polymers of this type, third and fourth aspects provide, respectively:

a) a poly(diallylamine) polymer comprising a repeat unit derived from a monomer of the general formula I below, or a pharmaceutically acceptable derivative of such a polymer, for use in any surgical, therapeutic or diagnostic method practised on a human or animal patient, in particular a method related to bile acid and/or serum cholesterol levels in the patient; and b) the use of such a polymer or derivative in the preparation of a medicament for use in any surgical, therapeutic or diagnostic method practised on a human or animal patient, in particular a method related to bile acid and/or serum cholesterol levels in the patient.

The term "therapy" as used here includes prophylaxis.

A fifth aspect of the invention provides a method of treatment of a human or animal patient to reduce bile acid levels and/or to reduce serum cholesterol levels, the method comprising administering to the patient a therapeutically effective amount of a poly(diallylamine) polymer comprising a repeat unit derived from a monomer of the general formula I, or of a pharmaceutically acceptable derivative of such a polymer.

According to a sixth aspect, the present invention provides a pharmaceutical composition containing, a poly(diallylamine) polymer comprising a repeat unit derived from a monomer of the general formula I, or a pharmaceutically acceptable derivative of such a polymer, together with a pharmaceutically acceptable excipient. The composition may also contain one or more other pharmaceutically active ingredients for co-administration. In accordance with the fifth aspect of the invention, the polymer may be present in the form of a pharmaceutical composition according to this sixth aspect.

In all aspects of the invention, the polymer may be either a homopolymer, a copolymer or a composite polymer of the type described below.

The monomer of the general formula I is shown below.

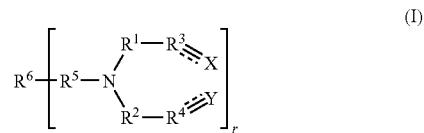

(I)

It may alternatively have the form shown below as Ia.

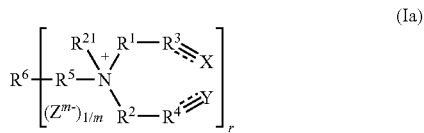

(Ia)

In formulae I and Ia, $R^1$ and $R^2$ are independently selected from $(CR^7R^8)_n$, or a group $CR^9R^{10}$, —$(CR^7R^8CR^9R^{10})$— or —$(CR^9R^{10}CR^7R^8)$— where n is 0, 1 or 2, $R^7$ and $R^8$ are independently selected from hydrogen or alkyl, $R^1$ and $R^2$ preferably being $CH_1$. One of $R^9$ or $R^{10}$ may be hydrogen and the other an electron withdrawing group, or $R^9$ and $R^{10}$ may together form an electron withdrawing group. $R^3$ and $R^4$ are independently selected from C, CH or $CR^{11}$ where $R^{11}$ is an electron withdrawing group, both preferably being CH. Where $R^1$ and/or $R^2$ are electron withdrawing, activating groups, suitable electron withdrawing groups $R^9$ and $R^{10}$ include $COCH_2CN$ and $COCH_3$, and preferably $R^9$ and $R^{10}$ together form an oxo group. Where $R^{11}$ is an electron withdrawing group, it is suitably $COCH_3$. The dotted lines indicate the presence or absence of a bond, preferably the absence, and X is a group $CX^1X^2$ where the dotted line bond to which it is attached is absent and a group $CX^1$ where the dotted line bond to which it is attached is present, Y is a group $CY^1Y^2$ where the dotted line bond to which it is attached is absent and a group $CY^1$ where the dotted line bond to which it is attached is present, and $X^1$, $X^2$, $Y^1$ and $Y^2$ are independently selected from hydrogen and fluorine. Preferably, $X^1$, $X^2$, $Y^3$ and $Y^4$ are all hydrogen.

$R^5$ is either a bond or an electron withdrawing group; $R^6$ is a bridging group of valency r; and r is an integer of 3 or greater, suitably of from 3 to 6, preferably 3 or 4.

$R^{12}$ is H, or an optionally substituted hydrocarbyl group, for instance an alkyl group such as a $C_{1-3}$ or $C_{3-24}$ alkyl. It is preferably a hydrophobic group such as a long chain (eg, a $C_3$-$C_{24}$) hydrocarbyl.

$R^6$ may be a straight or branched chain alkyl group, optionally substituted or interposed with functional groups or $R^6$ may comprise aromatic or heteroaromatic groups such as one or more unsaturated carbon rings, optionally containing heteroatoms such as nitrogen, oxygen or sulphur. $R^6$ may also be a tetra or octa substituted non-linear optic unit such as an optionally substituted porphyrin or phthalocyanine. $R^6$ may also be a polysiloxane network polymer comprising a straight or branched siloxane chain of valency r or a cyclic polysiloxane unit.

Z- is an anion of valency m, for example the conjugate base of a pharmaceutically acceptable acid, examples including halides (such as chloride or bromide), citrate, tartrate, lactate, phosphate, hydrophosphate, methanesulphonate, acetate, formate, maleate, fumarate, malate, succinate, malonate, sulphate, hydrosulphate, L-glutamate, L-aspartate, pyruvate, mucate, benzoate, glucuronate, oxalate, ascorbate and acetylglycinate. Other examples include fluoride, iodide, borides such as boron tetrafluoride; carboxylic acid esters such as those of formula $R^{14}C(O)O^-$ where $R^{14}$ is an optionally substituted hydrocarbyl group such as haloalkyl, in particular trifluoromethyl; and other anionic groups such as mesylate and tosylate.

Preferably, where $R^1$ and $R^2$ are both $(CR^7R^8)_n$, at least one n is 1 or 2. Suitably in formula I, n is 1 or 2.

On polymerisation of a compound of formula I or Ia, networks are formed whose properties may be selected depending upon the precise nature of the $R^6$ group, the amount of diluent, plasticiser or chain terminator present and the polymerisation conditions employed. Polymerisation will occur in accordance with the general scheme set out in the accompanying FIG. 1. Cross-linking in the polymer network occurs through the diene units, leading to a very stable material with robust physical properties.

Suitably the compound is designed such that it cyclopolymerises under the influence of ultraviolet or thermal radiation, preferably ultraviolet radiation. Cyclopolymerisation may take place either spontaneously in the presence of the appropriate radiation or in the presence of a suitable initiator, for example 2,2'-azobisisobutyronitrile (AIBN), aromatic ketones such as benzophenones in particular acetophenone; chlorinated acetophenones such as di- or tri-chloroacetophenone; dialkoxyacetophenones such as dimethoxyacetophenones (sold under the Trade name "Irgacure 651"); dialkylhydroxyacetophenones such as dimethylhydroxyacetophenone (sold under the Trade name "Darocure 1173"); substituted dialkylhydroxyacetophenone alkyl ethers such as compounds of formula

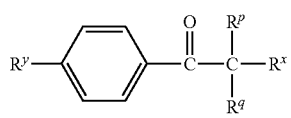

where $R^y$ is alkyl and in particular 2,2-dimethylethyl, $R^x$ is hydroxy or halogen such as chloro, and $R^p$ and $R^q$ are independently selected from alkyl or halogen such as chloro (examples of which are sold under the Trade names "Darocure 1116" and "Trigonal P1"); 1-benzoylcyclohexanol-2 (sold under the Trade name "Irgacure 184"); benzoin or derivatives such as benzoin acetate, benzoin alkyl ethers in particular benzoin butyl ether, dialkoxybenzoins such as dimethoxybenzoin or deoxybenzoin; dibenzyl ketone; acyloxime esters such as methyl or ethyl esters of acyloxime (sold under the trade name "Quantaqure PDO"); acylphosphine oxides, acylphosphonates such as dialkylacylphosphonate, ketosulphides for example of formula

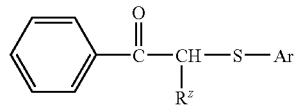

where $R^z$ is alkyl and Ar is an aryl group; dibenzoyl disulphides such as 4,4'-dialkylbenzoyldisulphide; diphenyldithiocarbonate; benzophenone; 4,4'-bis(N,N-dialkylamino)benzophenone; fluorenone; thioxanthone; benzil; or a compound of formula

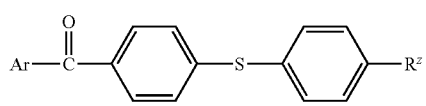

where Ar is an aryl group such as phenyl and $R^z$ is alkyl such as methyl (sold under the trade name "Speedcure BMDS").

The compound may be polymerised under the influence of a free radical or ion initiator as is understood in the art, as well as by application of an electron beam.

As used herein, the term "alkyl" refers to straight or branched chain alkyl groups, suitably containing from 1 to 20 and preferably from 1 to 6 carbon atoms. The terms "alkenyl" and "alkynyl" refer to unsaturated straight or branched chains which include for example from 2-20 carbon atoms, for example from 2 to 6 carbon atoms. Chains may include one or more double or triple bonds respectively. In addition, the term "aryl" refers to aromatic groups such as phenyl or naphthyl.

The term "hydrocarbyl" refers to any structure comprising carbon and hydrogen atoms. For example, these may be alkyl, alkenyl, alkynyl, aryl such as phenyl or napthyl, aralkyl, cycloalkyl, cycloalkenyl or cycloalkynyl. Suitably they will contain up to 20 and preferably up to 10 carbon atoms. The term "heterocyclyl" includes aromatic or non-aromatic rings, for example containing from 4 to 20, suitably from 5 to 10 ring atoms, at least one of which is a heteroatom such as oxygen, sulphur or nitrogen. Examples of such groups include furyl, thienyl, pyrrolyl, pyrrolidinyl, imidazolyl, triazolyl, thiazolyl, tetrazolyl, oxazolyl, isoxazolyl, pyrazolyl, pyridyl, pyrimidinyl, pyrazinyl, pyridazinyl, triazinyl, quinolinyl, iosquinolinyl, quinoxalinyl, benzthiazolyl, benzoxazolyl, benzothienyl or benzofuryl.

The term "functional group" refers to reactive groups such as halo, cyano, nitro, oxo, $C(O)_nR^a$, $OR^a$, $S(O)_tR^a$, $NR^bR^c$, $OC(O)NR^bR^c$, $C(O)NR^bR^c$, $OC(O)NR^bR^c$, $-NR^7C(O)_nR^6$, $-NR^aCONR^bR^c$, $-C=NOR^a$, $-N=CR^bR^c$, $S(O)_tNR^bR^c$, $C(S)_nR^a$, $C(S)OR^a$, $C(S)NR^bR^c$ or $-NR^bS(O)_tR^a$ where $R^a$, $R^b$ and $R^c$ are independently selected from hydrogen or optionally substituted hydrocarbyl, or $R^b$ and $R^c$ together form an optionally substituted ring which optionally contains further heteroatoms such as $S(O)_s$, oxygen and nitrogen, n is an integer of 1 or 2, t is 0 or an integer of 1-3. In particular the functional groups are groups such as halo, cyano, nitro, oxo, $C(O)_nR^a$, $OR^a$, $S(O)_tR^a$, $NR^bR^c$, $OC(O)NR^bR^c$, $C(O)NR^bR^c$, $OC(O)NR^bR^c$, $-NR^7C(O)_nR^6$, $-NR^aCONR^bR^c$, $-NR^aC-SNR^bR^c$, $-C=NOR^a$, $-N=CR^bR^c$, $S(O)_tNR^bR^c$, or $-NR^bS(O)_tR^a$ where $R^a$, $R^b$ and $R^c$, n and t are as defined above.

The term "heteroatom" as used herein refers to non-carbon atoms such as oxygen, nitrogen or sulphur atoms. Where nitrogen atoms are present, they will generally be present as part of an amino residue so that they will be substituted for example by hydrogen or alkyl.

The term "amide" is generally understood to refer to a group of formula C(O)NR$^a$R$^b$ where R$^a$ and R$^b$ are hydrogen or an optionally substituted hydrocarbyl group. The term "sulphonamide" correspondingly relates to groups of formula S(O)$_2$NR$^a$R$^b$.

An electron withdrawing group or groups may be used in compounds of formula I to activate one or more of the double bonds in preparation for polymerisation. The nature of each electron withdrawing group will depend upon its position in relation to the double bond it is required to activate, as well as the nature of any other functional groups within the compound.

In a preferred embodiment, the diallyl amino nitrogen and R$^5$ together form an electron withdrawing group. For example, they may represent a group such as N$^+$R$^{12}$(Z$^{m-}$)$_{1/m}$, such as in formula Ia. Alternatively, they may represent an amide or sulphonamide group where R$^5$ is a carbonyl or sulphonyl group such as C(O) or S(O)$_2$.

The properties of the polymer obtained from a monomer of formula I or Ia will depend upon a variety of factors. For instance, the nature of the anion Z will affect the physical properties of the polymer such as its porosity, water retention and conductivity. The nature of the group R$^6$ also has a significant effect. Suitably R$^6$ will comprise a bridging group for example as is known in polymer chemistry. It may include straight or branched chain alkyl groups, optionally substituted or interposed with functional groups or siloxane groups such as alkyl siloxanes.

Optionally the bridging group R$^6$ may be aromatic or heteroaromatic, i.e. it may include one or more unsaturated carbon rings, optionally containing heteroatoms such as nitrogen, oxygen or sulphur.

The length of the bridging group will affect the properties of the polymeric material derived from the monomer. This can be used to design polymers with properties which are best suited to the application. For instance when the bridging group comprises relatively long chains, (for example with in excess of 6 repeat units, for example from 6-20 repeat units), the polymer will have pliable plastic properties. Alternatively, when the bridging group is relatively short, (e.g. less than 6 repeat units) the material will be more brittle.

The poly(diallylamine) polymer used in the various aspects of the present invention may be a homopolymer, or a copolymer derived from a mixture of a monomer of formula I or Ia with another monomer. Many such other monomers are known in the art; they may themselves include diallylamine compounds.

The polymer may also be a composite produced by polymerising a compound of formula I or Ia in the presence of another moiety such as graphite, an ether such as a crown ether or thioether, a phthalocyanine or a bipyridyl, all of which can produce composite polymers with modified properties.

The group R$^6$ may be a bridging group comprising a tetra or octa substituted non-linear optic unit such as an optionally substituted porphyrin or phthalocyanine. Suitable optional substitutents in addition to the groups of formula I are hydrocarbyl groups such as alkyl in particular methyl. An example of such a compound is a compound of formula II:

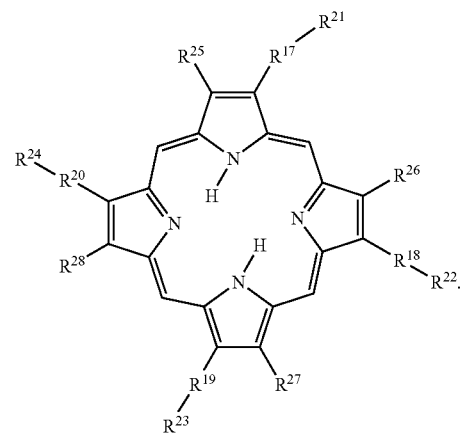

where R$^{21}$, R$^{22}$, R$^{23}$, and R$^{24}$ are each groups of sub-formula III

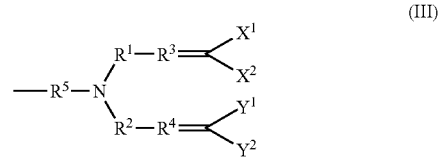

where X$^1$, X$^2$, Y$^1$, Y$^2$, R$^1$, R$^2$, R$^3$, R$^4$ and R$^5$ are as defined in relation to formula I;

R$^{25}$, R$^{26}$, R$^{27}$ and R$^{28}$ are each independently selected from hydrogen or hydrocarbyl groups such as alkyl and in particular methyl;

the compound optionally contains a metal ion such as magnesium or zinc, within the macrocyclic heterocyclic unit; and R$^{17}$, R$^{18}$, R$^{19}$ and R$^{20}$ are independently selected from groups of sub-formula IV:

$$—Z^1\text{-}(Q^1)_a\text{-}(Z^2\text{-}Q^2)_b\text{-}Z^3— \quad (IV)$$

where a and b are independently selected from 0, 1 or 2, Z$^1$, Z$^2$ and Z$^3$ are independently selected from a bond, an optionally substituted linear or branched alkyl or alkene chain wherein optionally one or more non-adjacent carbon atoms is replaced with a heteroatom or an amide group, Q$^1$ and Q$^2$ are independently selected from an optionally substituted carbocyclic or heterocyclic ring which optionally contains bridging alkyl groups.

Suitable carbocyclic rings for Q$^1$ and Q$^2$ include cycloalkyl groups for example of from 1 to 20 carbon atoms. Bridged carbocyclic ring structures include 1,4-bicyclo[2.2.2]octane, decalin, bicyclo[2.2.1]heptane, cubane, diadamantane, adamantane. Suitable heterocyclic rings include any of the above where one or more non adjacent carbon atoms are replaced by a heteroatom such as oxygen, sulphur or nitrogen (including amino or substituted amino), or a carboxyl or an amide group. Suitable optional substitutents for the groups Q$^1$ and Q$^2$ include one or more groups selected from alkyl, alkenyl, alkynyl, aryl, aralkyl such as benzyl, or functional groups as defined above. Particularly preferred substitutents for the groups Q$^1$ and Q$^2$ are oxo and halogen, in particular fluorine and chlorine.

Suitable optional substituents for the alkyl and alkene groups $Z^1$, $Z^2$ and $Z^3$ include aryl, aralkyl and functional groups as defined above. Particular substituents include halogens such as fluorine and chlorine, and oxo.

$R^{17}$, $R^{18}$, $R^{19}$ and $R^{20}$ may in particular be alkyl groups.

An alternative compound is a compound of formula V:

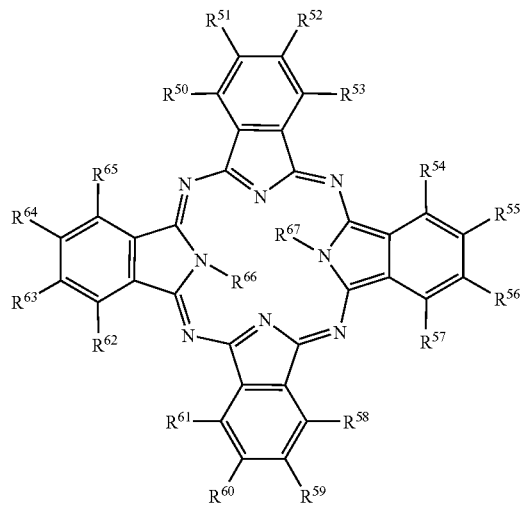

(V)

where $R^{50}$ through to $R^{65}$ are independently selected from hydrocarbyl in particular $C_{1-12}$ alkyl, a group $OR^{68}$ where $R^{68}$ is hydrocarbyl in particular butyl, halogen in particular chlorine, or a group $R^{21}$-$R^{24}$ where $R^{21}$ and $R^{24}$ are as defined in relation to formula II above, provided that at least three of $R^{50}$ to $R^{65}$ are $R^{21}$-$R^{24}$ groups; and $R^{66}$ and $R^{67}$ are either hydrogen or together comprise a metal ion such as a copper magnesium or zinc ion. Preferably in formula V, $R^{51}$, $R^{52}$, $R^{55}$, $R^{56}$, $R^{59}$, $R^{60}$, $R^{63}$ and $R^{64}$ are halogen and $R^{50}$, $R^{53}$, $R^{54}$, $R^{57}$, $R^{58}$, $R^{61}$, $R^{62}$ and $R^{65}$ are independently $C_{1-12}$ alkyl, $C_{1-12}$ alkoxy or a group $R^{21}$-$R^{24}$.

Polymerisation of a compound of formula II or V in accordance with the scheme of FIG. 1, for example by photopolymerisation, will provide a cross-linked network polymer where the cross-linking occurs through the diene units for example as either quaternery ammonium salts or amides depending upon the particular nature of the groups $R^5$ present in the $R^{21}$, $R^{22}$, $R^{23}$ and $R^{24}$ units. Again this can produce a very stable network or elastomeric material with robust physical properties. Pharmaceutically acceptable metals or metal ions may be inserted into the macrocyclic heterocyclic unit in order further to modify the polymer properties. Suitable metal ions include sodium, potassium, lithium, copper, zinc and iron ions. Yet a further possibility for a bridging group $R^6$ is a polysiloxane network polymer where $R^6$ comprises a straight or branched siloxane chain of valency r or a cyclic polysiloxane unit.

Thus the monomer of general formula I may have the structure VI:

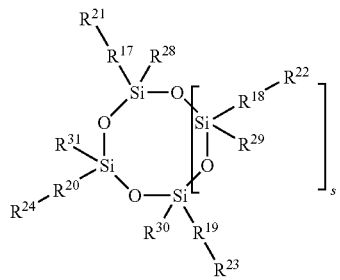

(VI)

where $R^{17}$, $R^{18}$, $R^{19}$, $R^{20}$, $R^{21}$, $R^{22}$, $R^{23}$ and $R^{24}$ are as defined above in relation to formula II;

$R^{28}$, $R^{29}$, $R^{30}$ are $R^{31}$ are $R^{31}$ are selected from hydrocarbyl such as alkyl and in particular methyl; and s is 0 or an integer of 1 or more, for example from 1 to 5.

In a particular embodiment, formula VI has four siloxane units in the ring (i.e. s is 1). It will be appreciated that there may be other numbers of such units in the cyclic ring, for example from 3 to 8 siloxane units (s is from 0 to 5), preferably from 3 to 6 siloxane units (s is from 0 to 3).

In the above structure VI, it will be appreciated that —Si— may be replaced by B or $B^-$; or —Si—O— may be replaced by —B—N($R^{40}$)— where $R^{40}$ is a hydrocarbyl group such as a group of formula $R^{19}$-$R^{23}$ as defined in relation to formula II.

Upon polymerisation, compounds of formula VI, or variants thereof, will form a cross-linked network where the cross-linking occurs through the groups $R^{21}$, $R^{22}$, $R^{23}$ and $R^{24}$ as illustrated in FIG. 1. Such polymers may be coated onto surfaces and polymerised in situ, for example using radiation curing.

Further examples of compounds of formula I include compounds of formula VII:

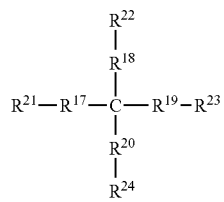

(VII)

where $R^{17}$, $R^{18}$, $R^{19}$, $R^{20}$, $R^{21}$, $R^{22}$, $R^{23}$ and $R^{24}$ are as defined above in relation to formula II.

Particular examples of compounds of formula I and related compounds are listed in Table 1 below.

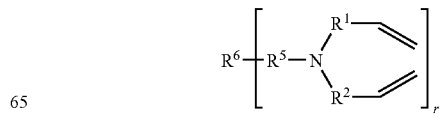

TABLE 1

| No. | R⁶ | R⁵ | R¹ | R² | r |
|---|---|---|---|---|---|
| 1 | >CH—CH< | C(O) | CH₂ | CH₂ | 4 |
| 2 | —CH₂CHCHCH₂— <br>   \| \| | CO | CH₂ | CH₂ | 4 |
| 3 | C[OC(O)(CH₂)₃—]₄ | CO | CH₂ | CH₂ | 4 |
| 4 | N[(CH₂)₂NHC(O)(CH₂)₃—]₃ | CO | CH₂ | CH₂ | 3 |
| 5 | N[(CH₂)₂OC(O)(CH₂)₃—]₃ | CO | CH₂ | CH₂ | 3 |
| 6 | 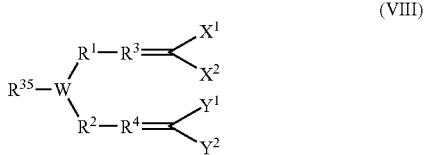 | CO | CH₂ | CH₂ | 3 |
| 7 | —CH₂C(OH)CH₂— <br>          \| <br>         C(O)— | CO | CH₂ | CH₂ | 3 | where — indicates a bond and Me is an abbreviation for methyl.

Particularly preferred polymers for use in the various aspects of the present invention are those derived from the monomers prepared in accordance with the experimental examples below. Compounds of formula I are suitably prepared by conventional methods, for example by reacting a compound of formula VIII:

(VIII)

where $X^1$, $X^2$, $Y^1$, $Y^2$, $R^1$, $R^2$, $R^3$ and $R^4$ are as defined in relation to formula I, W is a nitrogen atom or a substituted amine group as described above or a suitable precursor thereof, and $R^{35}$ is hydrogen or hydroxy, with a compound of formula IX:

$$R^6-[R^5-Z^4]_r \qquad (IX)$$

where $R^5$, $R^6$ and r are as defined in relation to formula I and $Z^4$ is a leaving group, and thereafter if desired or necessary converting a precursor group W to the desired amine form.

Suitable leaving groups $Z^4$ include halogen, in particular bromo, mesylate or tosylate. The reaction is suitably effected in an organic solvent such as tetrahydrofuran, dichloromethane, toluene, an alcohol such as methanol or ethanol, or a ketone such as butanone, and at elevated temperatures for example near the boiling point of the solvent.

Preferably the reaction is effected in the presence of a base such as potassium carbonate.

When the group W is a precursor of the desired amine, it may be converted to the desired form using conventional techniques. For example W may be a nitrogen atom, which may be converted to a group $NR^{12}(Z^{m-})_{1/m}$, where $R^{12}$, Z and m are as defined above, by reaction with an appropriate salt under conventional conditions.

Compounds of formulae VIII and IX are either known compounds or they can be prepared from known compounds by conventional methods.

The pharmaceutical composition of the sixth aspect of the invention may include pharmaceutically acceptable adjuvants such as carriers, buffers, stabilisers, coatings or other agents to prevent premature degradation or to delay release, taste masking agents or any other excipients, depending on the purpose of the composition and its intended route of administration (eg, oral, intravenous or whatever). It may additionally include other pharmaceutically active ingredients, which may be therapeutically (including prophylactically) active or have some diagnostic function. It may for instance contain one or more other bile acid removing agents.

The composition may be in any suitable form, such as a tablet, capsule, powder, solution or suspension. Conventional solid or liquid carriers may be used in such formulations. The concentration of the poly(diallylamine) polymer contained in the pharmaceutical composition will depend, of course, on the nature and severity of the condition to be treated or diagnosed using the composition, and on the patient to whom and method by which it is to be administered.

Possible uses for the pharmaceutical composition include both therapeutic and diagnostic uses. In particular, it may be used to treat and/or diagnose any condition which is related to (ie, which is or can be caused or mediated, directly or indirectly, by, or which is in any way associated with) the presence of bile acids, such as a high serum cholesterol level.

A therapeutic treatment method in which the poly(diallylamine) polymer may be used involves the administration to a patient suffering from a relevant condition of a therapeutically (which includes prophylactically) effective amount of the polymer, preferably in the form of a pharmaceutical composition according to the sixth aspect of the invention. "Effective amount" means an amount sufficient to cause a benefit (which may be prophylactic) to the patient or at least to cause a change in the patient's condition, ie, usually to cause a medically significant reduction in the patient's bile acid and/or serum cholesterol levels. The actual amount administered to the patient, and the rate and time-course of administration, will depend on the nature of the patient, the nature and severity of the condition, the administration method used, etc. . . . . Appropriate values can be selected by the trained medical practitioner. The polymer may be administered alone or in combination with other treatments, either simultaneously or sequentially. It may be administered by any suitable route, preferably orally. It may be administered directly to a suitable site or in a manner in which it targets a particular site—suitable targeting methods are already known.

A diagnostic method according to the invention might involve the use of the polymer or a derivative thereof, to determine, either qualitatively or quantitatively, the existence of a particular medical condition or change in condition. Such a method may be carried out either in vitro or in vivo. One or more of the materials used in the method may be appropriately labelled.

According to a seventh aspect of the present invention there is provided a method for producing a pharmaceutical composition according to the sixth aspect, said method comprising causing a monomer of formula I or Ia to polymerise. The resultant polymer may then be admixed with one or more pharmaceutically acceptable adjuvants, and/or with one or more other therapeutically or diagnostically active agents.

Suitably the monomer is a radiation curable compound and polymerisation is effected by subjecting the compound to the appropriate radiation (e.g. heat or ultraviolet radiation) and if necessary in the presence of a suitable initiator such as a photoinitiator like AIBN. Where the monomer cannot be cured in this way, or it would be inappropriate to do so, other conventional polymerisation techniques can be employed as would be understood in the art.

During the polymerisation process, the compounds of formula I or Ia link together by way of the unsaturated bonds such as the diene groups, as illustrated in FIG. 1. Because the compounds include at least two diene groups, they will tend to become cross-linked to form a network or three dimensional structure. The degree of cross-linking can be controlled by carrying out the polymerisation in the presence of cross-linkers, where for example r is 4, or diluents, plasticisers or chain terminators. These will suitably comprise a compound of formula X:

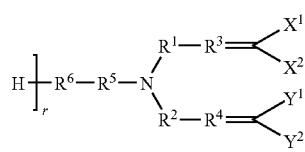
(X)

where $X^1$, $X^2$, $Y^1$, $Y^2$, $R^1$, $R^2$, $R^3$, $R^4$, $R^5$, $R^6$ and r are as defined in relation to formula I. Compounds of formula I may be used in the preparation of homopolymers, or of copolymers where they are mixed with other monomeric units which may themselves be of formula I or otherwise.

The polymers obtained from monomers of the general formula I or Ia have the general formula XI:

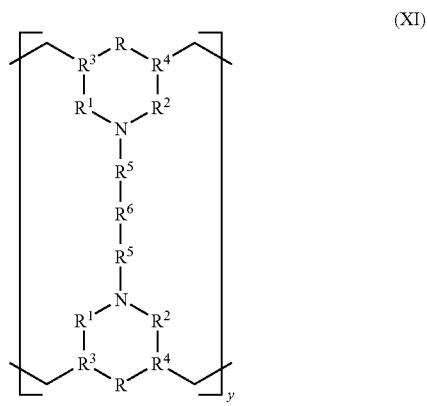
(XI)

where A is a bond or $CH_2$, $R^1$, $R^2$, $R^3$, $R^4$ and $R^5$ are as defined in relation to formula I, and $R^{6'}$ is a group of formula $R^6$ as defined in formula I which is substituted by at least one further group of sub formula XII:

where y is an integer in excess of 1, preferably in excess of 5 and suitably from 5 to 30 and A is as defined above. It will be understood that copolymers also fall within the scope of this definition as outlined above.

To form the polymers of use in the present invention, it is possible to take a suitable organic system that has optimal or optimised properties for use in a desired application and to

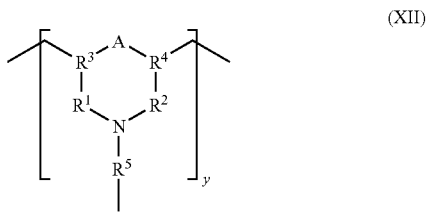
(XII)

structurally modify the system by the incorporation of diallylamino groups, thus introducing not only bile acid sequestering properties but also a ready ability to polymerise, in particular using heat or light curing. A three dimensional network can then be created that will have properties associated with the parent organic system.

An advantage of working with monomers of formula I is that they may be applied to a desired substrate and caused to polymerise in situ, thus increasing ease of processing.

A further advantage is their versatility, allowing a wide range of desired physicochemical properties to be built into the polymers formed from them. In particular, either amorphous or ordered systems can be prepared depending upon the polymerisation conditions used. Copolymerisation can also be used to affect the physical properties of the end product. Systems can be prepared which mimic conventional polymers, or which involve donor/acceptor systems.

The polymers can be produced in a range of physical forms, including films and coatings, using heat or radiation curing techniques if desired.

The invention will now be particularly described by way of example with reference to the accompanying diagrammatic drawings in which:

FIG. 1 illustrates the way in which compounds of the general formula I may cyclopolymerise to form polymers of use in the present invention.

The following experimental examples illustrate the preparation of monomers of the general formula I and polymers derived from them, which polymers may be used in the various aspects of the present invention.

Example 1

Preparation and Polymerisation of Compound No. 1 in Table 1

Step 1

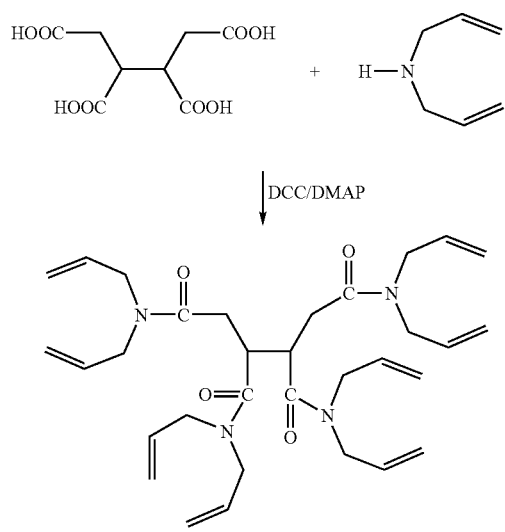

Meso-butan-1,2,3,4-tetracarboxylic acid (20.0 g, 0.0428 mol), diallylamine (39.0 g, 0.20 mol), 1,3-dicyclohexylcarbodiimide (82.50 g, 0.20 mol) and 4-dimethylaminopyridine (2.0 mg) were dissolved in dichloromethane/tetrahydrofuran (1:1) mixture (200 cm3) and the mixture was stirred at room temperature for 120 hours. 1,3-dicyclohexylurea was removed by filtration and the solvent removed in vacuo to leave a yellow oil. Column chromatography (silica gel/ethyl acetate) followed by removal of solvent in vacuo gave a heavy pale yellow oil which solidified on standing. 42.3 g, 89%.

$^1$HNMR (CDCl$_3$) δ: 2.90 (m, 4H), 3.50 (m, 2H), 3.80 (m, 16H), 5.20 (m, 16H), 5.70 (m, 8H)

Ir vmax (thin film): 3323, 3086, 2935, 2861, 1650, 1545, 1416, 1363, 1228, 1135, 994, 925, 556 cm$^{-1}$ Step 2

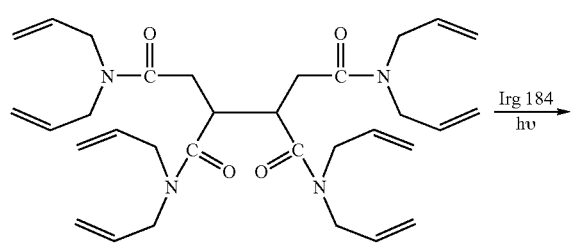

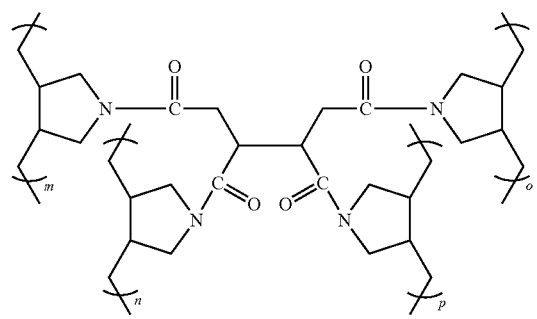

Monomer from Step 1 (1.0 g) was dissolved in dry dichloromethane (3 cm$^3$). The Irgacure 184 (10 mg) was added to the solution, heated and mixed to ensure homogenicity. It was then spread evenly on an 18×25 cm glass plate and the solvent allowed to evaporate off to leave a thin, clear film. This was irradiated with a Philips UVA sunlamp for 30 minutes to form a hard cross-linked polymer film. This was removed (scalpel), washed in dichloromethane and dried. Yield 0.64 g, 64%.

Ir vmax (thin film): 3424, 2936, 2374, 2346, 1705, 1644 (s), 1524, 1436 (s), 1222, 1138, 992, 924, 561 cm$^{-1}$ Example 2

Preparation of Compound No. 3 in Table 1

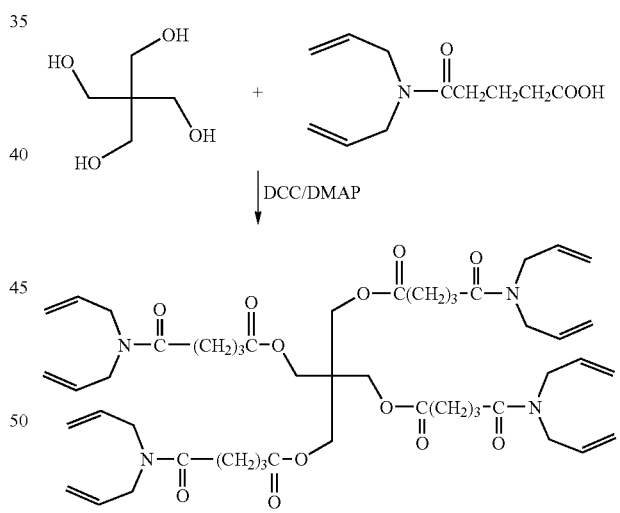

Amide A (23.21 g, 0.11 mol), pentaerythritol (3.75 g, 0.028 mol), dicyclohexylcarbodiimide (22.70 g, 0.11 mol) and 4-dimethylaminopyridine (0.50 g) were placed in THF/dichloromethane mixture (1:1) and left stirring at room temperature for 5 days. The resultant dicyclohexylurea was removed by filtration and the solvent removed in vacuo to leave a yellow oil. Column chromatography using silica gel and ethyl acetate followed by methanol gave, after removal of solvent in facuo 23.6 g, 95% of pale yellow oil.

Ir vmax (thin film): 2938, 1743 (s), 1649 (s), 1417, 1225, 1149, 996, 926, 559 cm$^{-1}$.

$^1$HNMR(CDCl$_3$) δ: 1.95 (quin, 8H), 2.40 (quartet, 16H), 3.88 (d, 8H), 3.97 (d, 8H), 4.10 (s, 8H), 5.16 (m, 16H), 5.77 (m, 8H).

Example 3

Preparation of Compound No. 4 in Table 1

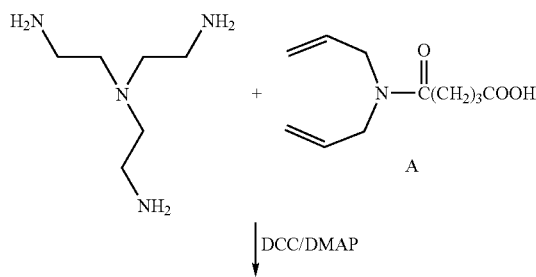

Tris(2-aminoethyl)amine (2.08 g, 0.0142 mol) and dicyclohexylcarbodiimide (8.87 g, 0.043 mol) were placed in dry dichloromethane (100 cm$^3$) and stirred at room temperature. Amide A (9.0 g, 0.043 mol) in dry dichloromethane (20 cm$^3$) was added dropwise over 30 minutes and the whole was left to stir for five days. The dicyclohexylurea was removed by filtration (Whatman No. 1 filter paper) and the solvent removed in vacuo to leave a yellow oil. The oil was purified using chromatography (ethyl acetate followed by methanol). Removal of solvent gave a pale yellow oil, 8.94 g, 87%.

Ir νmax (thin film): 3321 (s), 3086, 2934, 1620, 1551, 1420, 1358, 1234, 1136, 1060, 994, 927, 756, 665, 560 cm$^{-1}$.

$^1$HNMR (CDCl$_3$) δ: 1.95 (quin, 6H), 2.28 (t, 6H), 2.41 (t, 6H), 2.56 (t, 6H), 3.26 (q, 6H), 3.95 (d, 6H), 3.96 (d, 6H), 5.14 (m, 12H), 5.75 (m, 6H), 7.28 (t, 3H).

Example 4

Preparation of Compound No. 5 in Table 1

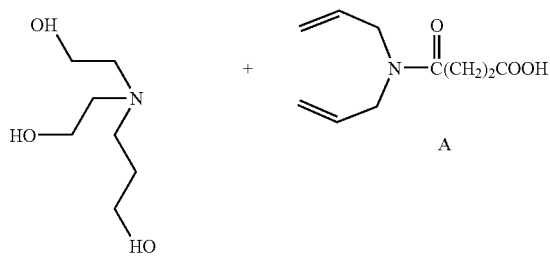

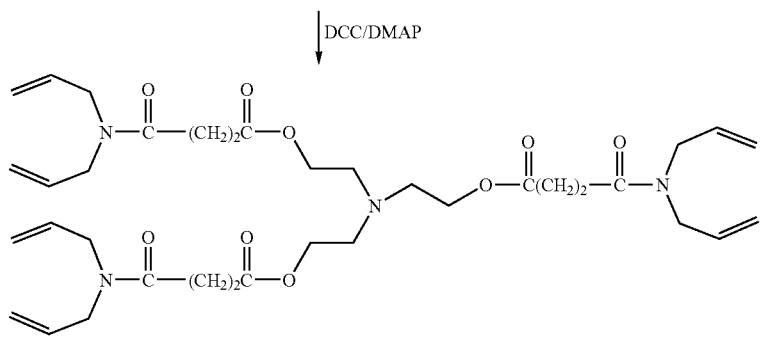

-continued

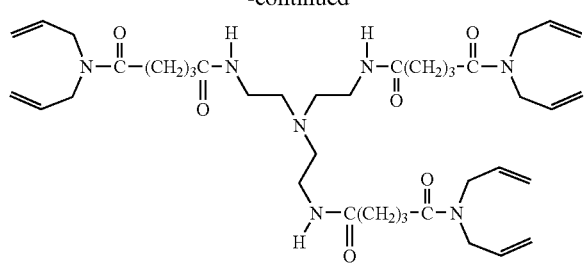

Triethanolamine (5.10 g, 0.034 mol), Amide A (20.0 g, 0.10 mol), dicyclohexylcarbodiimide (20.60 g, 0.10 mol) and 4-dimethylaminopyridine (0.5 g) were dissolved in dry dichloromethane and the solution stirred for 48 hours. The resultant dicyclohexylurea was removed by filtration and the solvent removed in vacuo to leave a yellow oil. The oil was redissolved in dichloromethane and washed with 3M HCl solution (100 ml), then brine (100 ml), then dried over MgSO$_4$. The solvent was removed in vacuo to leave an oil which was purified via column chromatography using silica gel with ethyl acetate as the eluent. Removal of solvent in vacuo left 21.4 g, 91% as a pale yellow oil.

Ir νmax (thin film): 3087, 2932, 1738, 1654, 1416, 1223, 1169, 995, 927, 755, 666, 557 cm$^{-1}$.

$^1$HNMR(CDCl$_3$) δ: 2.65 (m, 12h), 2.85 (t, 6H), 3.90 (d, 6H), 3.98 (d, 6H), 4.13 (t, 6H), 5.10 (m, 12H), 5.76 (m, 6H).

Example 5

Preparation of Compound No. 6 in Table 1

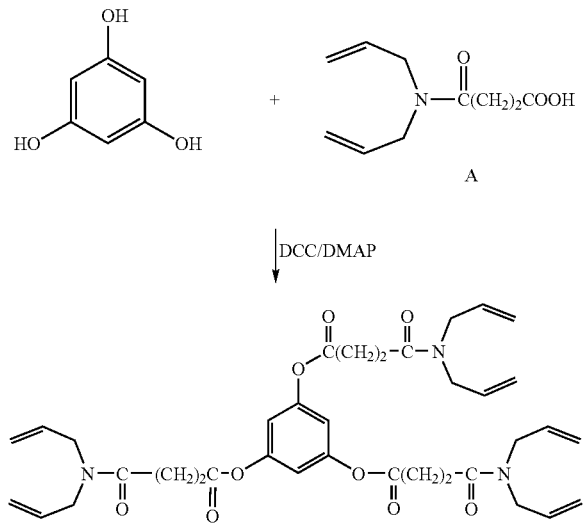

Phlorglucinol dihydrate (5.0 g, 0.031 mol), amide A (15.43 g, 0.095 mol), dicyclohexylcarbodiimide (19.60 g, 0.095 mol) and 4-dimethylaminopyridine (0.5 g) were placed in dry dichloromethane and stirred for 48 hours at room temperature. Dicyclohexylurea was removed by filtration and the solvent removed in vacuo to leave a clear oil. Column chromatography using silica gel and ethyl acetate followed by removal of solvent in vacuo gave a clear oil, 16.40 g, 76%.

Ir vmax (thin film): 3088, 3016, 2932, 1769 (s), 1656 (s), 1417, 1369, 1226, 1131, 997, 927, 756, 667, 556 cm$^{-1}$.

$^1$HNMR (CDCl$_3$) δ: 2.72 (t, 6H), 2.88 (t, 6H), 3.91m, 6H), 4.00 (m, 6H), 5.15 (m, 12H), 5.76 (m, 6H), 6.80 (s, 3H).

Example 6

Preparation of Compound No. 7 in Table 1

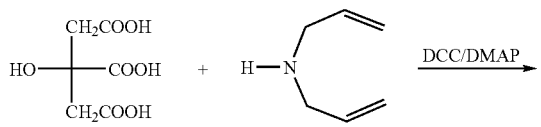

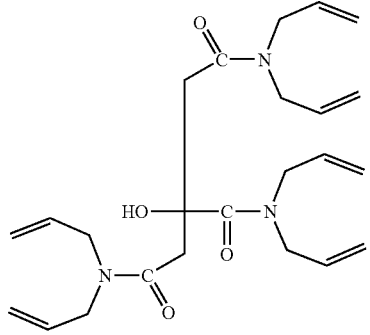

Citric acid (10.0 g, 0.048 mol) and diallylamine (14.0 g, 0.145 mol) were carefully placed in 25 cm$^3$THF-Dichloromethane (1:1) and stirred for 30 minutes. Dicyclohexylcarbodiimide (25 cm3) (30.0 g, 0.145 mol) was added slowly and carefully to the reaction mixture. Finally 4-dimethylaminopyridine (1.0 g) was added and the mixture was stirred at room temperature for 8 days. Thin layer chromatography (ethyl acetate) showed a major new product and several smaller ones. The dicyclohexylurea was removed by filtration (Whatman No. 1 filter paper) and the solvent removed in vacuo to leave a yellow oil. The oil was redissolved in dichloromethane (150 cm$^3$) and washed with (i) 3M HCl solution (100 cm$^3$), (ii) 3M Na$_2$CO$_3$ solution (100 cm$^3$), (iii) brine (100 cm$^3$), then dried over MgSO$_4$. Removal of solvent in vacuo left a yellow oil which was dried thoroughly to leave 12.37 g, 58% of product.

Ir vmax (thin film): 3294, 3086, 2987, 1737 (w), 1637 (s), 1400 1345, 1228, 1137, 995, 921, 756, 690 cm$^{-1}$.

$^1$HNMR (CDCl$_3$) δ: 2.24 (s, 4H), 3.20 (s, br, 1H), 3.88 (d, 6H), 3.99 (d, 6H), 5.20 (m, 12H), 5.78 (m, 6H).

Example 7

Preparation of Polymer Composite

Compound A

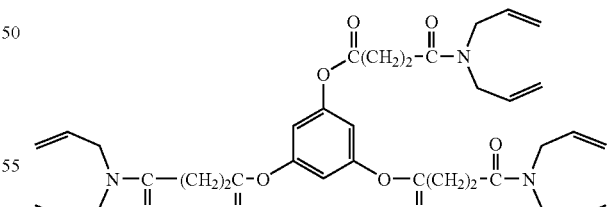

+

-continued

CH₂=CH-CH₂-N(-CH₂-CH=CH₂)-C(=O)-C(CF₂)₃COOH

↓ Irgacure 184/hv (Hard Lacquer) → Polymer (on glass)

Compound B

Monomers A (0.5 g) and B (0.025 g) were dissolved with the Irgacure 184 (25 mg) in dry dichloromethane (2 cm³) and the solution spread over an area 3×7 cm on a plate glass plate. The solvent was allowed to evaporate to leave a thin monomer film which was irradiated with a Philips UVA (75w) sunlamp for 1 hour. The resultant hard polymer film was washed with dry dichloromethane (20 cm³) to remove surface stickiness and allowed to dry in air.

The invention claimed is:

1. A pharmaceutical composition containing a poly(diallylamine) polymer, wherein all diallyl nitrogen atoms are linked to at least two further diallyl nitrogen atoms, said polymer comprising a repeat unit of a monomer of formula Ia:

$$\left[ R^6 + R^5 - \underset{(Z^{m-})_{1/m}}{\overset{R^{12}}{\underset{N^+}{\bigg\backslash}}} \underset{R^2-R^4}{\overset{R^1-R^3}{\bigg/}} \underset{Y}{\overset{X}{\Bigg\langle}} \right]_r \quad (Ia)$$

wherein $R^1$ and $R^2$ are independently selected from $(CR^7R^8)_n$, or a group $CR^9R^{10}$, —$(CR^7R^8CR^9R^{10})$— or —$(CR^9R^{10}CR^7R^8)$— where n is 0, 1 or 2, $R^7$ and $R^8$ are independently selected from hydrogen or alkyl, and either (a) one of $R^9$ or $R^{10}$ is hydrogen and the other an electron withdrawing group given by $COCH_2CN$ or $COCH_3$, or (b) $R^9$ and $R^{10}$ together form an oxo electron withdrawing group;

$R^3$ and $R^4$ are independently selected from C, CH or $CR^{11}$, where $R^{11}$ is an electron withdrawing group given by $COCH_3$;

the dotted lines indicate the presence or absence of a bond, and X is a group $CX^1X^2$ where the dotted line bond to which it is attached is absent and a group $CX^1$ where the dotted line bond to which it is attached is present, Y is a group $CY^1Y^2$ where the dotted line bond to which it is attached is absent and a group $CY^1$ where the dotted line bond to which it is attached is present, and $X^1, X^2, Y^1$ and $Y^2$ are independently selected from hydrogen and fluorine;

$R^5$ is either a bond or an electron withdrawing group;

$R^6$ is selected from an aromatic group, a heteroaromatic group, a tetra substituted non-linear optic unit, an octa substituted non-linear optic unit, or a straight or branched chain alkyl group, optionally substituted or interposed with functional groups, a polysiloxane polymer network bridging group of valency r;

r is an integer of 3 or greater;

$R^{12}$ is H, or an optionally substituted hydrocarbyl group;

m is a positive integer; and $Z^-$ is an anion of valency m, or a pharmaceutically acceptable derivative of such a polymer, together with a pharmaceutically acceptable excipient.

2. A pharmaceutical composition according to claim 1 wherein in formula Ia, $R^1$ and $R^2$ are both $CH_2$.

3. A pharmaceutical composition according to claim 1, wherein in formula Ia, $R^3$ and $R^4$ are both CH.

4. A pharmaceutical composition according to claim 1 wherein in formula Ia, $X^1, X^2, Y^3$ and $Y^4$ are all hydrogen.

5. A pharmaceutical composition according to claim 1 wherein in formula Ia, r is from 3 or 4.

6. A pharmaceutical composition according to claim 1 wherein in formula Ia, $R^{12}$ is a hydrophobic group.

7. A pharmaceutical composition according to claim 1 wherein in formula Ia, $R^1$ and/or $R^2$ are electron withdrawing, activating groups.

8. A pharmaceutical composition according to claim 1 wherein in formula Ia, $Z^-$ is chloride or bromide.

9. A pharmaceutical composition according to claim 1 wherein in formula Ia, the diallyl amino nitrogen and $R^5$ together form an electron withdrawing group.

10. A pharmaceutical composition for producing a pharmaceutical composition according to claim 1, the method comprising causing a monomer of formula Ia to polymerize, and admixing the resultant polymer with one or more pharmaceutically acceptable adjuvants.

11. A pharmaceutical composition according to claim 10 wherein the compound of formula Ia is able to cyclopolymerise under the influence of ultraviolet or thermal radiation.

12. A method of treatment of a human or animal patient to reduce bile acid levels, the method comprising administering to the patient a therapeutically effective amount of the poly (diallylamine) polymer of claim 1 or of a pharmaceutically acceptable derivative of such a polymer.

13. A composition according to claim 1 wherein the heteroaromatic comprises one or more unsaturated carbon rings, optionally containing heteroatoms such as nitrogen, oxygen or sulphur.

14. A composition according to claim 1 wherein $R^6$ is an optionally substituted porphyrin or phthalocyanine.

15. A composition according to claim 1 where $R^6$ comprises a straight or branched siloxane chain of valency r or a cyclic polysiloxane unit.

* * * * *